United States Patent [19]

McCaskill

[11] 4,420,551

[45] Dec. 13, 1983

[54] NOVEL BENZOTRIAZINE DEVELOPERS AND PHOTOGRAPHIC PRODUCT AND METHOD

[75] Inventor: Emmett S. McCaskill, Wellesley, Mass.

[73] Assignee: Polaroid Corporation, Cambridge, Mass.

[21] Appl. No.: 450,373

[22] Filed: Jan. 31, 1983

[51] Int. Cl.³ .................. G03C 5/54; G03C 1/48; G03C 5/30; G03C 1/06
[52] U.S. Cl. .................................. 430/234; 430/249; 430/405; 430/440; 430/483; 430/566
[58] Field of Search ............ 430/234, 249, 440, 483, 430/566, 405

[56] References Cited

U.S. PATENT DOCUMENTS 3,574,621  4/1971  Schaller et al. ............... 430/483

OTHER PUBLICATIONS

"Organic Electrosyntheses ... Esters", Falsig et al. *Acta Chemica Scandinavica* B31 (1977), pp. 15-20, No. 1.

*Primary Examiner*—Richard L. Schilling
*Attorney, Agent, or Firm*—Gaetano D. Maccarone

[57] ABSTRACT

This application relates to the use of certain dihydro-benzotriazine compounds as photographic silver halide developing agents and to photographic processes, products and compositions which utilize the same. The compounds are effective developers in acid environment as well as in basic environment. Also described are novel dihydro-benzotriazine compounds.

8 Claims, 1 Drawing Figure

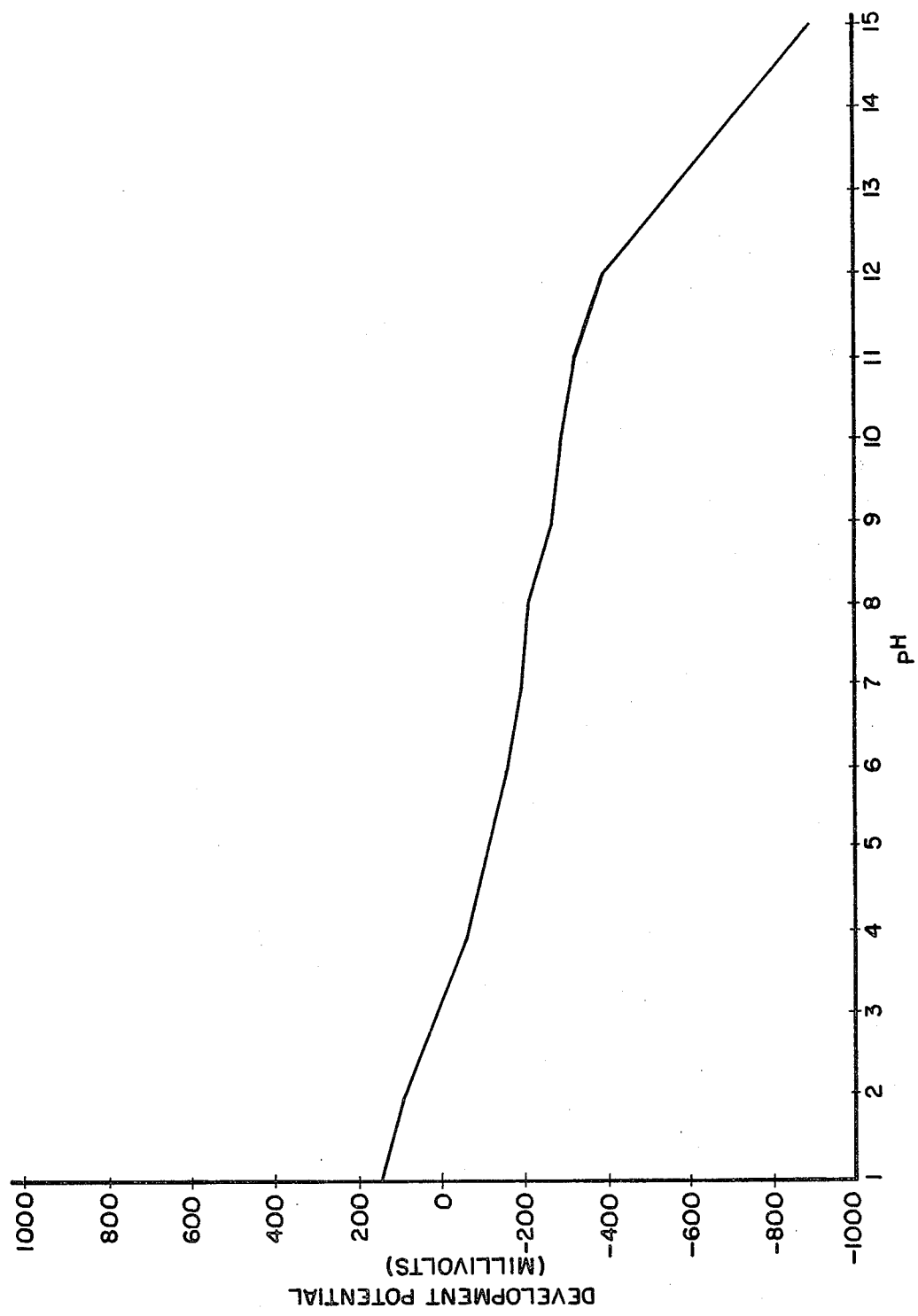

4,420,551

NOVEL BENZOTRIAZINE DEVELOPERS AND PHOTOGRAPHIC PRODUCT AND METHOD

BACKGROUND OF THE INVENTION

This invention relates to photography and, more particularly, to compounds, products and processes which are useful in the development of photosensitive silver halide emulsions.

It is known in the art that the pH range in which a photographic developing agent is effective and the dependence of activity on pH can vary greatly from one developing agent to another. Many organic developing agents show useful activity only in alkaline solution although some are active in slightly acid solution. Other developers such as the vanadous ion developers can only be used in strongly acid solution, while still others, such as the ferrous ion complex with ethylenediaminetetraacetic acid, are sufficiently stable against hydrolysis to be used in alkaline as well as in acid solution.

The present invention is directed to photographic products and processes which utilize certain dihydrobenzotriazine compounds which are useful as silver halide developing agents in acid and alkaline media and to novel dihydro-benzotriazine compounds.

SUMMARY OF THE INVENTION

It is therefore an object of this invention to provide novel photographic products and processes.

It is another object of the invention to provide photographic products and processes which utilize silver halide developing agents which are effective in acid and alkaline media.

Still another object of the invention is to provide photographic products and processes wherein the silver halide developing agent is generated in situ.

Yet another object is to provide photographic products and processes wherein a silver halide developing agent is formed by electrochemical reduction of a precursor.

A further object is to provide novel dihydrobenzotriazine compounds.

BRIEF SUMMARY OF THE INVENTION

These and other objects and advantages are accomplished in accordance with the invention by providing photographic products and processes which employ a silver halide developing agent represented by the formula

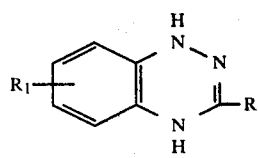

FORMULA A wherein R is H, alkyl, preferably having from 1 to 6 carbon atoms, alkoxy, preferably having from 1 to 6 carbon atoms or aryl such as phenyl; and $R_1$ is H, alkyl, preferably having from 1 to 6 carbon atoms, —$CF_3$, —COOH, —$NH_2$, —$NHSO_2R_2$ or —$OR_2$ where $R_2$ is alkyl, preferably having from 1 to 6 carbon atoms.

The compounds wherein R is —$CH_3$ or —$C_2H_5$ and $R_1$ is H are reported in Acta Chemica Scandanavica B 31(1977) No. 1, pp 15-20. The other compounds are novel compounds.

BRIEF DESCRIPTION OF THE DRAWING

The accompanying FIGURE is a graphical illustration of the development potential vs pH for one silver halide developer of the invention as measured for approximately $5 \times 10^{-4}$ molar concentrations of the compound in buffered pH solutions.

DESCRIPTION OF THE PREFERRED EMBODIMENTS

Compounds which are preferred for use according to the invention are represented by the formulas

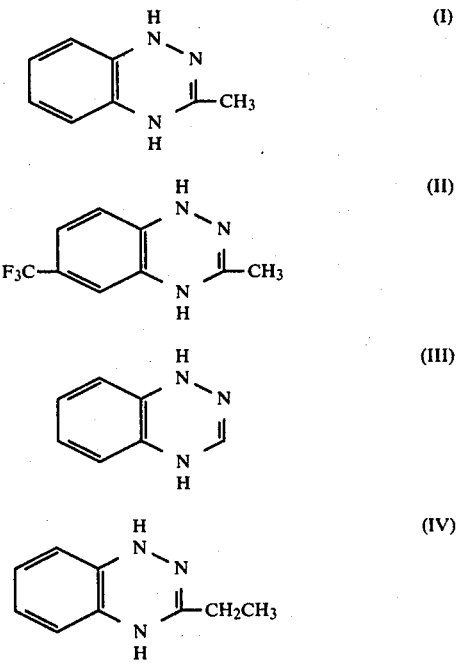

The compounds which are utilized according to the invention can be prepared by reactions which are known in the art. For example, a benzotriazole having an appropriate substituent, if desired, on the benzene ring can be electrochemically reduced in a 4 N HCl-ethanol medium to provide an aminohydrazine which is then condensed with an appropriate ortho ester to give the desired product. The reaction proceeds according to the following sequence:

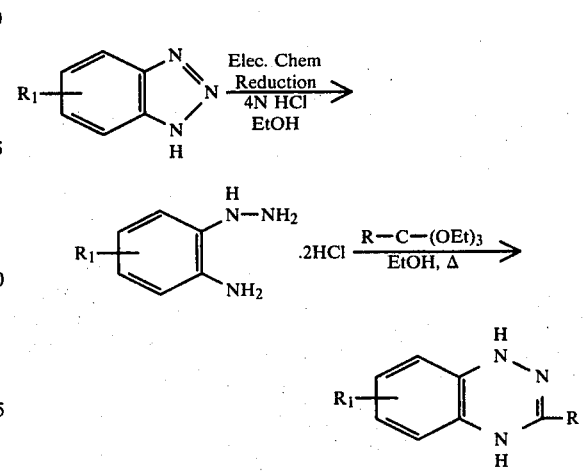

As indicated above the compounds within Formula A are typically effective silver halide developers in acid and alkaline media. The FIGURE illustrates the development potential vs pH for Compound I as measured with approximately $5 \times 10^{-4}$ molar concentrations in buffered pH solutions. It ca be seen that the compound is effective as a silver halide developer over a pH range of from about 3 to about 10.

These silver halide developing agents are useful in conventional or "tray" development and are particularly useful in diffusion transfer processes for forming images in silver or in color. Such processes are well known in the art. See, for example, U.S. Pat. Nos. 2,543,181; 2,647,056; 2,983,606 and 3,719,489. In processes of this type an exposed silver halide emulsion is treated with a processing composition whereby the exposed silver halide emulsion is developed and an imagewise distribution of diffusible image-forming components is formed in the unexposed and undeveloped portions of the silver halide emulsion. This distribution of image forming components is transferred by imbibition to an image receiving stratum in superposed relationship with the silver halide emulsion to provide the desired transfer image.

In silver diffusion transfer processes, processing of the exposed silver halide emulsion is effected in the presence of a silver halide solvent, such as sodium thiosulfate or uracil, which forms a diffusible complex with the undeveloped silver halide. The soluble silver complex thus formed diffuses to the superposed image-receiving layer where the transferred silver ions are deposited as metallic silver to provide the silver transfer image.

In preparing silver prints in this manner, the image-receiving layer preferably includes certain materials, the presence of which, during the transfer process has a desirable effect on the amount and character of silver precipitated on the image-receiving element. Materials of this type are specifically described in U.S. Pat. Nos. 2,690,237; 2,698,245; and 3,671,241.

The photosensitive element may be any of those conventionally used in silver diffusion transfer processes and generally comprises a silver halide emulsion carried on a base, e.g., glass, paper or plastic film. The silver halide may be a silver chloride, iodide, bromide, iodobromide, chlorobromide, etc. The binder for the halide, though usually gelatin, may be a suitable polymer such as polyvinyl alcohol, polyvinyl pyrrolidone and their copolymers.

Separating the photosensitive element from the image-receiving layer may be controlled so that the layer of processing composition is removed from the image-receiving layer or the layer of processing composition is caused to remain in contact with the image-receiving layer, e.g., to provide it with a protective coating. Techniques which enable such results to be accomplished as desired are described in U.S. Pat. No. 2,647,054. In general, the processing reagents are selected so that traces remaining after the solidified processing layer has been separated from the silver image or which remain in said layer adhered as a protective coating on the silver image are colorless or pale, so as not to appreciably affect the appearance of the image and to have little or no tendency to adversely react with the silver image.

The developing agents of the present invention also may be employed in diffusion transfer processes adapted to provide positive silver transfer images which may be viewed as positive transparencies without being separated from the developed negative silver image including such processes adapted for use in forming additive color projection positive images. Diffusion transfer processes of this type are described in U.S. Pat. Nos. 3,536,488; 3,615,428; and 3,894,871.

The subject developing agents also may be employed in diffusion transfer processes where the final image is in dye, and as appropriate for the particular color process, the developing agent may be used as the principal developer, for example, in the processes of aforementioned U.S. Pat. No. 3,719,489 or as an auxiliary developer, for example, in the processes of aforementioned U.S. Pat. No. 2,983,606. In these diffusion transfer processes, a photosensitive component comprising at least one photosensitive silver halide emulsion having a dye image-providing compound associated therewith in the same or in an adjacent layer is exposed to form a developable image and then developed with a processing composition to form an imagewise distribution of a soluble and diffusible image-providing material which is transferred, at least in part, by diffusion, to a superposed image-receiving component comprising at least a dyeable stratum. These processes rely for color image formation upon a differential in mobility or solubility of dye image-providing material obtained as a function of development so as to provide an imagewise distribution of such material which is more diffusible and which, therefore, may be selectively transferred to the superposed dyeable stratum. The differential in mobility or solubility may be obtained, for example, by a chemical reaction such as a redox reaction, a silver ion assisted cleavage reaction or a coupling reaction.

The image dye-providing materials which may be employed in such processes generally may be characterized as either (1) initially soluble or diffusible in the processing composition but which are selectively rendered nondiffusible imagewise as a function of development; or (2) initially insoluble or nondiffusible in the processing composition but which selectively provide a diffusible product imagewise as a function of development. The image dye-providing materials may be complete dyes or dye intermediates, e.g., color couplers.

Examples of initially soluble or diffusible materials and their use in color diffusion transfer processes are disclosed, for example, in U.S. Pat. Nos. 3,087,817; 2,661,293; 2,693,244; 2,698,798; 2,802,735; and 2,983,606. Examples of initially non-diffusible materials and their use in color transfer systems are disclosed in U.S. Pat. Nos. 3,443,939; 3,443,940; 3,227,550; 3,227,551; 3,227,552; 3,227,554; 3,243,294; 3,445,228; 3,719,488 and 3,719,489.

In any of these systems, multicolor images may be obtained by employing a photosensitive element containing at least two selectively sensitized silver halide layers each having associated therewith a dye image-providing material exhibiting the desired spectral absorption characterisitics. The most commonly employed elements of this type are the so-called tripack structures employing a blue-, a green- and a red-sensitive silver halide layer having associated therewith, respectively, a yellow, a magenta and a cyan image-providing material.

The photosensitive and image-receiving elements may be separate components which are brought together during processing and thereafter retained together as the final print or separated following image formation; or they may together comprise a unitary structure. e.g., an integral negative-positive film structure wherein the the negative and positive, i.e., the photosensitive element and image-receiving element are laminated and/or otherwise physically retained together at least prior to image formation. Integral negative-positive film structures adapted for forming color transfer images viewable without separation, i.e. wherein the image-receiving component containing the dye transfer image need not be separated from the photosensitive component for viewing purposes are described and claimed in U.S. Pat. Nos. 3,415,644; 3,415,645; 3,415,646; 3,573,043; 3,573,044; 3,594,164; and 3,594,165.

In conventional development and in diffusion transfer photographic processes, the subject compounds may be used as the sole silver halide developing agent, or they may be employed in combination with another silver halide developing agent as an auxiliary developer or as the main component of the developing combination. Examples of developing agents that may be used in combination with the subject compounds include hydroquinone and substituted hydroquinones, such as, tertiary butyl hydroquinone, 2,5-dimethyl hydroquinone, methoxyhydroquinone, ethoxyhydroquinone, chlorohydroquinone; pyrogallol and catechols, such as catechol, 4-phenyl catechol and tertiary butyl catechol; aminophenols, such as 2,4,6-triaminophenol, 2,4-diaminophenol dihydrochloride and 4,6-diamino-ortho-cresol; 1,4-diaminobenzenes, such as, p-phenylenediamine, 1,2,4-triaminobenzene and 4-amino-2-methyl-N,N-diethylaniline; ascorbic acid and its derivatives, such as, ascorbic acid, isoascorbic acid and 5,6-isopropylidene ascorbic acid; and hydroxylamines, such as N,N-di-(2-ethoxyethyl)hydroxylamine and N,N-(di-2-methoxyethoxyethyl)hydroxylamine.

When the compounds of the present invention are used in diffusion transfer processes, the processing composition if it is to be applied to the emulsion by being spread thereon in a thin layer usually includes a film-forming thickening agent. The processing composition may comprise, for example, one or more developing agents of the present invention and optionally, one or more conventional developing agents such as those enumerated above, an alkali such as sodium hydroxide or potassium hydroxide including a buffer to control the pH and a viscosity-increasing agent such as a high molecular weight polymer e.g., sodium carboxymethyl cellulose, hydroxyethyl cellulose, or carboxymethyl hydroxyethyl cellulose. As noted above, in the production of a silver transfer image, a silver halide solvent is employed which may be included in the processing composition, or if desired, a silver halide solvent precursor such as those disclosed in U.S. Pat. No. 3,698,898 may be disposed in a layer of the film unit. In addition to the above ingredients, the processing composition may be further modified by the inclusion of restrainer, preservatives and other components commonly employed in developer compositions. All these materials are preferably in aqueous solution.

Rather than being dissolved in the aqueous processing composition prior to application thereof to an exposed silver halide emulsion, the developing agents of the present invention may be disposed prior to exposure in the photosensitive element, e.g., by placing them in, on or behind a silver halide emulsion layer. In this instance, the processing composition containing the developing agent is formed by application to the photosensitive element of an aqueous solution capable of solubilizing the developing agent. In diffusion transfer processes, the subject developing agents usually are contained in the processing composition. Whether the developing agent is initially disposed in the processing composition or in the photosensitive element, upon application of the processing composition, the developing agent is provided for processing the photoexposed silver halide material.

It will be apparent that the amount of the developing agents may be varied to suit the requirements of a given photographic system. Routine scoping tests may be used to ascertain the concentration appropriate for any given photographic system. Also, where it is desirable, it is contemplated to include in the processing compositions other components as commonly used in the photographic art.

Further, as mentioned above, rather than being dissolved in the aqueous processing composition prior to application thereof to an exposed silver halide emulsion, it is also contemplated that the developing agents may be disposed prior to exposure in a layer or layers of the photographic film unit, e.g., by placing them in or behind a silver halide emulsion layer in the photosensitive element. In this instance the processing composition containing the developing agent is formed by application to the photosensitive element of an aqueous solution capable of solubilizing the developing agent.

In one embodiment of the invention the dihydrobenzotriazine silver halide developers are formed in situ by converting the corresponding benzotriazine compound electrochemically to the desired dihydro-benzotriazine. Upon the application of a reducing potential the benzotriazine is reduced to the corresponding dihydro-benzotriazine and development of the exposed photosensitive element takes place.

The invention will now be described in detail with respect to specific preferred embodiments by way of examples, it being understood that these are intended to be illustrative only and the invention is not intended to be limited to the materials. conditions, process parameters, etc. recited therein.

EXAMPLE I

Velox F photographic paper (available from Eastman-Kodak) was exposed on a sensitometer to a step wedge for $2 \times 10^{-4}$ second and then developed in a pH 3.0 buffer solution of compound I (about 0.1 M in compound I) for 30 seconds. The exposed paper was rinsed vigorously with water to remove the developer and stop development. The paper was fixed with a general purpose hardening fixer followed by rinsing and drying. A well developerd image was obtained.

The procedure was repeated with a 60-second development time. Again, a well developed image was obtained.

EXAMPLE II

A photosensitive element, Polaroid Corp. Type 107, was exposed (approximately 0.01 sec.) to a step wedge and processed with a processing composition comprising

| hydroxyethyl cellulose | 0.1g |
|---|---|
| $Na_2S_2O_3$ | 0.2g |
| Compound IV | 0.1g |
| pH 12.0 buffer | 10 ml | as the photosensitive element was passed, in superposed relationship with a Polaroid Corp. Type 107C image receiving element, through a pair of rollers at a gap spacing of about 0.0026 inch. After an imbibition period of 60 seconds, the photosensitive and image receiving elements were separated. An image was visible in the image receiving element indicating that unreduced silver halide had transferred to the image receiving element.

EXAMPLE III

A photosensitive element was formed consisting of a support made up of a transparent polymeric layer carrying a thin evaporated gold layer (Intrex G-Type 28 FX available from Sierracin Corp.) on which there was coated a silver halide emulsion layer coated at a coverage of about 1292 mgs/m² of silver. The photosensitive element was exposed to a gray scale in the dark and then utilized as the cathode in an electrochemical cell which contained 20 ml of a pH 5.0 buffer solution which was approximately $10^{-1}$ to $10^{-2}$ molar in 1,2,4-benzotriazine, a gold wire counter electrode and a saturated KCl salt bridge with a SCE reference electrode.

A reducing potential of −500 millivolts (vs SCE) was applied to the photosensitive element for 30 minutes (100 microamps current). The photosensitive element was then removed from the cell, washed with water and dried. A visible image was obtained in the exposed areas and no image was observed on the unexposed areas.

The experiment was repeated with 2-methyl-1,2,4-benzotriazine. Again, a visible image was obtained.

Although the invention has been described with respect to various specific preferred embodiments, it is not intended to be limited thereto but rather those skilled in the art will recognize that variations and modifications may be made therein which are within the spirit of the invention and the scope of the claims.

What is claimed is:

1. A method of developing a silver halide emulsion which comprises treating an exposed silver halide emulsion layer carried on a support with an aqueous processing composition including a silver halide developing agent represented by the formula

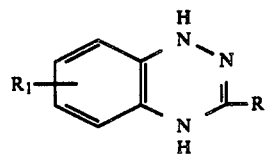

wherein R is H, alkyl, alkoxy or aryl, $R_1$ is H, alkyl, $-CF_3$, $-COOH$, $-NH_2$, $-NHSO_2R_2$ or $-OR_2$, and $R_2$ is alkyl.

2. The method as defined in claim 1 wherein R is alkyl having from 1 to 6 carbon atoms.

3. The method as defined in claim 1 wherein said silver halide developing agent is in a layer of a photosensitive element including said silver halide emulsion and said solution of said developing agent is formed by applying to said photosensitive element an aqueous solution in which said developing agent is soluble.

4. The method as defined in claim 1 wherein said processing composition includes a silver halide solvent and said silver halide emulsion is developed in the presence of an image-receiving material superposed on said emulsion to form a silver transfer image on said image-receiving material.

5. The method as defined in claim 1 wherein said silver halide developing agent is formed by electrochemical reduction of a precursor.

6. A photographic product comprising a support, a silver halide emulsion carried on said support and a developing agent in a layer on the same side of said support as said silver halide emulsion, said developing agent represented by the formula

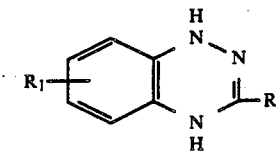

wherein R is H, alkyl, alkoxy or aryl, $R_1$ is H, alkyl, $-CF_3$, $-COOH$, $-NH_2$, $-NHSO_2R_2$ or $-OR_2$, and $R_2$ is alkyl.

7. The product as defined in claim 6 wherein R is alkyl having from 1 to 6 carbon atoms.

8. The product as defined in claim 6 and further including a silver halide solvent and a layer of an image receiving material.

* * * * *